United States Patent
Liesfeld et al.

(10) Patent No.: US 9,532,712 B2
(45) Date of Patent: Jan. 3, 2017

(54) OPHTHALMOSCOPE HAVING A LASER DEVICE

(75) Inventors: Ben Liesfeld, Potsdam (DE); Winfried Teiwes, Kleinmachnow (DE); Ulrike Weber, Potsdam (DE); Kay-Uwe Amthor, Potsdam (DE); Stephan Kirsch, Birkenwerder (DE)

(73) Assignee: OD-OS GmbH, Teltow (DE)

( * ) Notice: Subject to any disclaimer, the term of this patent is extended or adjusted under 35 U.S.C. 154(b) by 3 days.

(21) Appl. No.: 13/497,491

(22) PCT Filed: Sep. 29, 2010

(86) PCT No.: PCT/EP2010/006031
§ 371 (c)(1),
(2), (4) Date: Jun. 1, 2012

(87) PCT Pub. No.: WO2011/038935
PCT Pub. Date: Apr. 7, 2011

(65) Prior Publication Data
US 2012/0239015 A1    Sep. 20, 2012

Related U.S. Application Data

(60) Provisional application No. 61/246,757, filed on Sep. 29, 2009.

(30) Foreign Application Priority Data

Sep. 29, 2009  (EP) .................................... 09075449

(51) Int. Cl.
*A61B 18/18*    (2006.01)
*G02C 3/00*    (2006.01)
(Continued)

(52) U.S. Cl.
CPC . *A61B 3/14* (2013.01); *A61B 3/12* (2013.01); *A61F 9/00821* (2013.01); *A61F 9/008* (2013.01);
(Continued)

(58) Field of Classification Search
CPC ............ A61F 9/008; A61F 2009/00872; A61F 9/00804; A61F 2009/00887; A61F 2009/0087; A61F 9/00821; A61B 3/14; A61B 3/12; A61B 3/145
(Continued)

(56) References Cited

U.S. PATENT DOCUMENTS 4,248,505 A    2/1981  Muchel et al.
4,452,517 A    6/1984  Kohayakawa
(Continued)

FOREIGN PATENT DOCUMENTS

DE    3001244 A1    7/1980
EP    0791361 A2    8/1997
(Continued)

OTHER PUBLICATIONS

European Search Report issued in EP Application No. 06116853, dated Apr. 24, 2007.
(Continued)

*Primary Examiner* — Lynsey Crandall
*Assistant Examiner* — Sebastian X Lukjan
(74) *Attorney, Agent, or Firm* — Faegre Baker Daniels LLP

(57) ABSTRACT

An ophthalmoscope having a laser device for laser irradiation of an eye, in particular for performing a photocoagulation on fundus of the eye of the eye, includes an illuminator for illuminating the eye as well as a camera for acquiring an image of the eye. The illuminator is adapted to generate visible and infrared lights. The ophthalmoscope
(Continued)

further includes a control unit adapted to trigger the illuminator for generating a light pulse of visible light and to read out from the camera a control image of the eye acquired by the camera during the light pulse. The ophthalmoscope is configurable to acquire an image of an eye and perform a laser treatment of an eye.

27 Claims, 4 Drawing Sheets

(51) Int. Cl.
A61B 3/14 (2006.01)
A61B 3/12 (2006.01)
A61F 9/008 (2006.01)

(52) U.S. Cl.
CPC .... A61F 9/00804 (2013.01); A61F 2009/0087 (2013.01); A61F 2009/00844 (2013.01); A61F 2009/00863 (2013.01); A61F 2009/00872 (2013.01); A61F 2009/00887 (2013.01)

(58) Field of Classification Search
USPC .................................. 606/4–6, 11; 351/206
See application file for complete search history.

(56) References Cited

U.S. PATENT DOCUMENTS

| | | | |
|---|---|---|---|
| 4,666,268 A | 5/1987 | Ito | |
| 5,279,298 A * | 1/1994 | Flower | 600/321 |
| 5,430,506 A | 7/1995 | Volk | |
| 5,526,189 A | 6/1996 | Heacock | |
| 5,912,720 A | 6/1999 | Berger et al. | |
| 6,159,202 A * | 12/2000 | Sumiya et al. | 606/4 |
| 6,247,812 B1 | 6/2001 | Miehle et al. | |
| 6,478,424 B1 * | 11/2002 | Grinvald | A61B 3/12 351/206 |
| 6,758,564 B2 | 7/2004 | Ferguson | |
| 8,100,531 B2 | 1/2012 | Liesfeld et al. | |
| 8,545,020 B2 | 10/2013 | Liesfeld et al. | |
| 8,545,021 B2 | 10/2013 | Liesfeld et al. | |
| 8,545,022 B2 | 10/2013 | Liesfeld et al. | |
| 9,055,896 B2 | 6/2015 | Amthor et al. | |
| 2001/0005225 A1 | 6/2001 | Clark et al. | |
| 2002/0099363 A1 | 7/2002 | Woodward et al. | |
| 2003/0144650 A1 * | 7/2003 | Smith | 606/5 |
| 2003/0208189 A1 * | 11/2003 | Payman | 606/5 |
| 2005/0105044 A1 | 5/2005 | Warden et al. | |
| 2006/0114544 A1 | 6/2006 | Bloom et al. | |
| 2006/0285075 A1 * | 12/2006 | Matsumura | 351/206 |
| 2007/0055222 A1 * | 3/2007 | Hohla et al. | 606/12 |
| 2007/0216909 A1 * | 9/2007 | Everett et al. | 356/479 |
| 2008/0165322 A1 * | 7/2008 | Su et al. | 351/211 |
| 2008/0278683 A1 | 11/2008 | Su et al. | |
| 2009/0244482 A1 | 10/2009 | Elsner et al. | |
| 2010/0007849 A1 | 1/2010 | Liesfeld et al. | |
| 2012/0089133 A1 | 4/2012 | Liesfeld et al. | |
| 2012/0165905 A1 | 6/2012 | Liesfeld et al. | |
| 2012/0165906 A1 | 6/2012 | Liesfeld et al. | |
| 2012/0274901 A1 | 11/2012 | Amthor et al. | |

FOREIGN PATENT DOCUMENTS

| | | |
|---|---|---|
| EP | 1389943 A2 | 2/2004 |
| WO | WO9101703 A1 | 2/1991 |
| WO | WO9905853 A1 | 2/1999 |
| WO | WO0195791 A1 | 10/2001 |
| WO | WO02094088 A2 | 11/2002 |

OTHER PUBLICATIONS

European Search Report issued in EP Application No. 09075449, Dated Jan. 26, 2010.
European Search Report issued in EP Application No. 09075450, mailed Feb. 8, 2010.
International Search Report and Written Opinion issued in PCT/EP2007/056967 mailed Jan. 29, 2008.
International Search Report and Written Opinion issued in PCT/EP2010/006031, mailed Mar. 10, 2001.
International Search Report and Written Opinion issued in PCT/EP2010/006037, mailed May 11, 2010, 14 pages.
Kaiser, Richard S. et al., "Laser Burn Intensity and the risk for Choroidal Neovascularization in the CNVPT Fellow Eye Study", Ophtalmologie, Paris; vol. 119, Jun. 1, 2001, pp. 826-832.
Parel, Jean-Marie et al., "Review Article: The Optics of the Ophthalmoscope and Related Instruments", Journal of Physics E. Scientific Instruments, vol. 13, No. 12, Dec. 1, 1980, pp. 1242-1253.
Yannuzzi, L.A. et al., "ophthalmic fundus imaging: today and beyond", American Journal of Ophthalmology, vol. 137, No. 3, Mar. 1, 2004, pp. 511-524.

* cited by examiner

OPHTHALMOSCOPE HAVING A LASER DEVICE

CROSS-REFERENCE TO RELATED APPLICATION(S)

This application claims priority to PCT Patent Application No. PCT/EP2010/006031, filed Sep. 29, 2010, which claims priority to U.S. Provisional Application No. 61/246,757, filed Sep. 29, 2009, and European Patent Application No. 09075449.0, filed Sep. 29, 2009, which are herein incorporated by reference in their entirety.

TECHNICAL FIELD

The present invention relates to an ophthalmoscope. More particularly, the present invention relates to an ophthalmoscope having a laser device for laser irradiation of an eye and a camera for acquiring an image of the eye.

BACKGROUND

Ophthalmoscopes having laser devices are frequently used for the observation and treatment of eyes. Therein, photocoagulation represents an important method of treatment wherein the fundus of the eye, also referred to as fundus, is coagulated or sclerosed. In order to successfully perform such a treatment it is necessary to position a therapeutic laser beam exactly on the region to be treated. Moreover, an effect of a laser treatment on a treated tissue in the eye has to be controlled and verified.

To this end, the eye to be treated is usually illuminated with visible light during laser therapy. This has the advantage that under visible (white) light a physiological effect of the laser treatment, which as a rule becomes manifest in the form of bleaching of the irradiated tissue, is particularly distinctly visible. In particular, even before laser treatment a test laser irradiation of the eye is therefore experimentally carried out in uncritical regions of the eye in order to perform, under white light illumination, a determination of optimum irradiation duration, irradiation intensity and further parameters.

However, most patients find illumination of the eye with visible light to be dazzling and extremely unpleasant so that the patients concerned often react to the illumination with instinctive ocular movements. These ocular movements considerably complicate observing as well as acquiring an image of the eye. The ocular movements have a particularly adverse effect on the accuracy with which laser irradiation can be applied to a desired region to be treated, thus causing a considerable risk of unintended irradiation of a sensitive region of the eye. In addition, ocular movements as a rule require new positioning of a laser beam, which can result in a considerable extension of treatment duration, in particular if a great number of regions of the eye have to be irradiated individually.

As a result, it is customary to place a contact glass onto the cornea of the eye and in this way to mechanically suppress said ocular movements. However, this leads to irritations of the eye, and as a rule is feasible under local anesthetic only.

SUMMARY OF THE INVENTION

In one aspect, an ophthalmoscope having a laser device for laser treatment of an eye includes an illuminator for illuminating the eye and configured to generate visible and infrared light. The ophthalmoscope also includes a camera for acquiring an image of the eye, and a control unit configured to trigger the illuminator to generate a light pulse of visible light, and to read out from the camera a control image acquired by the camera during the light pulse.

In another aspect, a method for laser treatment of an eye includes laser irradiating the eye with a laser device, and illuminating the eye with an the illuminator for a predetermined waiting time interval after laser irradiating the eye. The method further includes triggering the illuminator to generate a light pulse of visible light and acquiring a control image of the eye with a camera during the light pulse.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
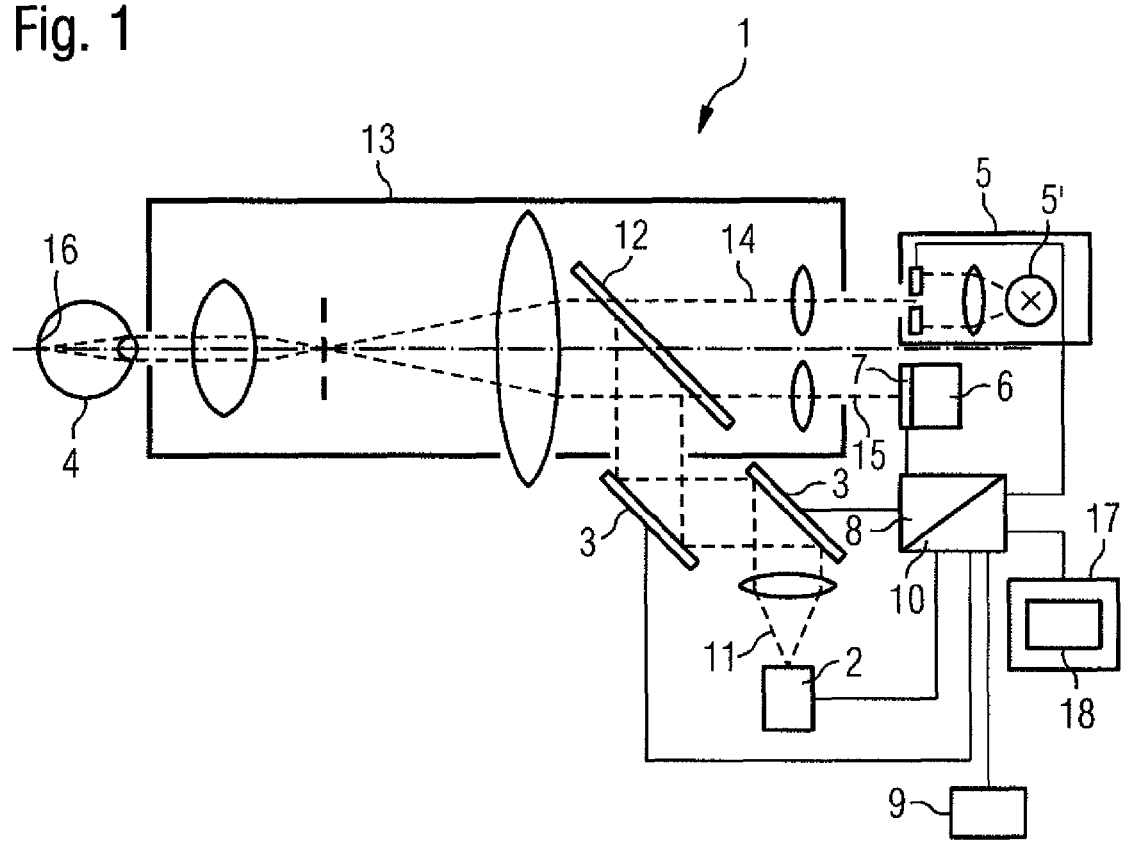
FIG. 1 is a schematic representation of the exemplary embodiment of ophthalmoscope proposed herein.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a schematic representation of a specific embodiment of an ophthalmoscope 1 of the type proposed herein. It comprises a laser device 2 having a beam guiding unit 3 for the laser irradiation of an eye 4. The ophthalmoscope further comprises an illuminator 5 for the illumination of the eye 4 optionally with infrared and/or visible light by means of light-emitting diodes 5', a camera 6 having a CCD sensor 7 being sensitive to infrared light as well as to visible light, and a control unit 8 connected to the camera 6. The control unit 8 is adapted to trigger the illuminator 5 for generating a light pulse of visible light after a waiting time interval of 200 ms after laser irradiation of the eye 4 with a therapeutic laser beam, and to read out from the camera 6 a control image of the eye 4 acquired by the camera 6 during the light pulse, cf. FIG. 2 to FIG. 5.

The control unit 8 is further adapted to trigger the illuminator 5 for generating the light pulse also before laser irradiation of the eye 4 with a therapeutic laser beam, and to read out from the camera 6 another control image as a reference image. Additionally, the control unit 8 is connected to an input interface 9 for inputting a trigger signal wherein the control unit 8 is adapted to trigger the illuminator 5 for generating the light pulse after the input of the trigger signal, and to read out from the camera 6 the control image acquired by the camera 6 during the light pulse.

An image processing unit 10 is integrated into the control unit 8, which is connected to the camera 6 via the control unit, and is adapted for real time processing of image signals of the camera 6.

The image processing unit 10 is further adapted to select and magnify an image detail of a control image, and to partly superimpose the control image with the selected and magnified image detail, wherein the selected and magnified image detail comprises a region of the eye treated with laser irradiation. Moreover, the image processing unit 10 is adapted to generate a difference value image from a pair of control images. To this end, the image processing unit 10 is equipped with a memory to store the control images, and further being adapted to carry out a feature based image registration of these both control images.

The beam guiding unit 3 is particularly adapted to guide out a laser beam 11 of the laser device 2, which is optionally given by a target laser beam, the therapeutic laser beam or a superimposition of both, during the light pulse of visible light from an observation range acquired by the camera (6). A beam splitter 12 serves for coupling the laser beam 11 into an optical system 13, which serves for forming an image of an illuminating beam 14 originating from the illumination system 5 and of a target or a therapeutic laser beam 11 superimposing the illuminating beam onto the eye 4, onto a fundus 16 of the eye 4, in the case at hand. Moreover, the optical system 13 simultaneously serves for forming an image of an observation beam 15 onto the sensor 7 of the camera 6 wherein the observation beam is given by the reflection of the illuminating beam 14 (and the laser beam 11 in the case that the laser beam is not deflected by the beam guiding unit as described above) on the eye 4.

An observation device 17 having a screen 18 is connected to the control unit 8 and the image processing unit 10 integrated in the control unit 8 for the optical representation of the images of fundus of the eye 16 acquired by the camera 6.

According to the following FIGS. 2 through 5 a method of acquiring a control image of the fundus 16 will be described which is carried out with the exemplary embodiment 1 of the invention described herein. Moreover, a method of the execution of a photocoagulation will be described which is carried out with the embodiment 1 on the fundus 16 of the eye as well. The numbering of the features of the embodiment 1 is then maintained.

Figure 2:
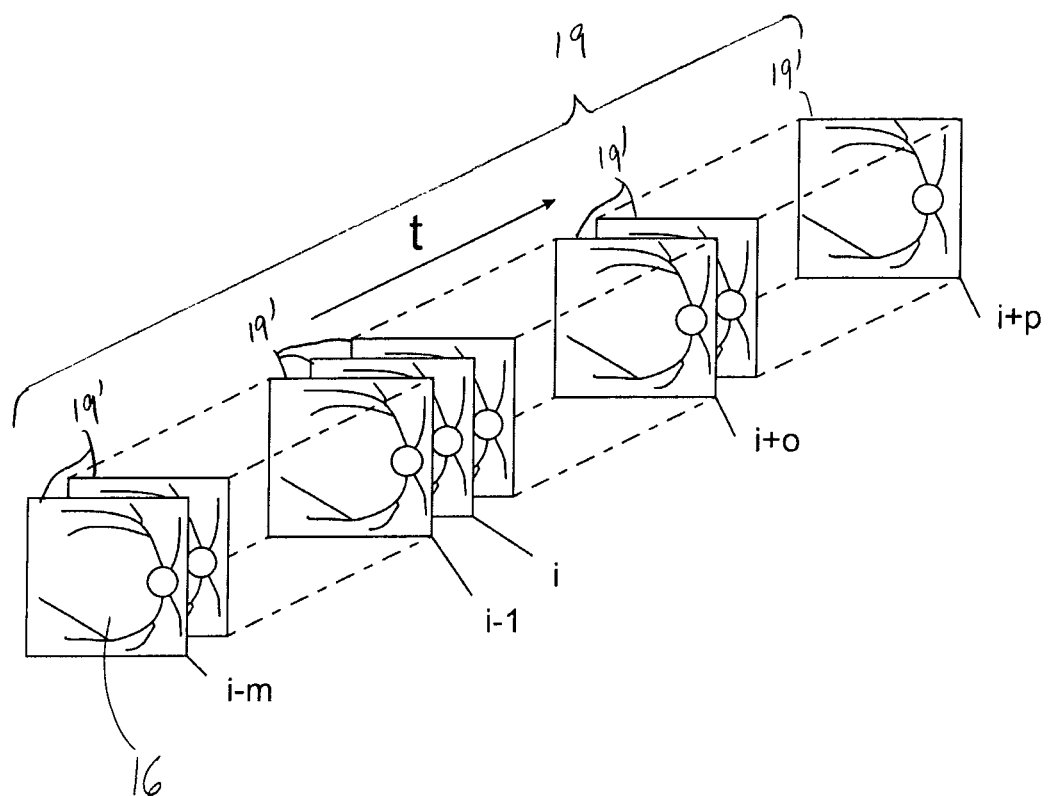
FIG. 2 is a time sequence of images of a fundus of an eye.

FIG. 2 shows a schematic representation of a time sequence 19 of images 19' which have been taken by the embodiment described according to FIG. 1. The arrow indicated with the letter t as well as the indexings of i−m, i−1, i, i+o and i+p show then the direction and the order of the time sequence 19 of images 19' wherein the indices i, m, o and p are positive integers. Furthermore, it applies that p is greater than or equal to o.

For the generation of this image sequence 19, the eye 4 is continuously irradiated by means of the illuminator 5 with an infrared invisible illuminating beam 14. With the optical system 13 this illuminating beam 14 is imaged onto the fundus 16 of the eye 4, and the reflection thereof on the fundus 16 which is given by the observation beam 15, is imaged onto the sensor 7 of the camera 6. The sensor 7 generates a time sequence of image signals which are forwarded by the camera 6 to the image processing unit 10 integrated in the control unit 8. Finally, these image signals are transferred from the image processing unit to the observation device 17 which displays the image signals on the screen 18 as a time sequence 19 (as a real time image). In the present embodiment, a picture taking rate of the camera 6 is about 25 Hz, i.e. a related exposure time of the individual images 19' is about 40 ms.

In a method of generating a control image of the eye 4 the control unit 9 activates the illuminator to generate a light pulse which is adapted of duration as short as possible in order to prevent eye dazzling. In principle, as a result it is sufficient to limit the duration of the light pulse to the exposure time of the individual images 19' of the image sequence 19 since a unique one of the images 19' is sufficient as a control image. The light pulse is generated, for example, during the exposure time of image 19' having the index i. This image 19' having the index i is read out now as control image of eye 4 from the camera. Subsequently, the control image is stored by the image processing unit 10 as the case may be and/or processed, forwarded to the observation device 17 and displayed by the screen 18. Such a method can be actuated by the operator for example by operating the input interface 9.

Therapeutic laser irradiation of an eye 4 with the therapeutic laser beam 3 has usually a duration in the range between 10 ms and 1000 ms, and may thus be longer than the exposure time of the individual images 19'. In the following exemplary method of performing a laser treatment of the eye 4, during exposure time of the image 19' having index i, an irradiation of fundus of the eye 16 has started with a therapeutic laser beam having a pulse duration of 400 ms. The index i+o marks the first image which is taken after completion of the irradiation. In this embodiment, thus o has a value of 11 since irradiation is finished during the exposure time of the image having index i+10=i. As described above, the control unit 8 or in the present embodiment the image processing unit 10 integrated therein is adapted to read out a control image from the camera after a predetermined waiting time interval has elapsed after laser irradiation. In the case at hand this waiting time interval is 120 ms. This means, that in the present embodiment (with the picture taking rate of 40 Hz) applies o+3=14. In this embodiment the image 19' read out as control image from the image sequence 19 has the index i+p=i+14. During the exposure time of the image 19' having index i+p, being the control image, the laser beam 11 which is set as target laser at this time will be deflected off by the laser guiding device 2 from the sensor's field of vision and thus in particular from the irradiated location in the fundus of the eye such that the image information of this location will not be superimposed by the target laser beam. Moreover, during taking the control image, the eye is illuminated with visible light automatically such that a lesion of the tissue of fundus of the eye 16 caused by the laser irradiation becomes visible on the control image at the irradiated location as a bleaching.

Moreover, the control unit 8 reads out from the camera another control image serving as a reference image a predetermined time interval before the laser irradiation. To this end, the control unit 8 comprises a memory serving as a circular buffer which will be continuously filled with images 19' dating back temporally at least up to the above mentioned time interval. At the time of triggering laser irradiation an image 19' having an index being related to the time interval is read out as a reference image from the circular buffer. In this embodiment this time interval amounts to 160 ms such that the reference image carries the index i−m=i−4. During the exposure time of this image 19' fundus of the eye is also illuminated with visible light in order to compare the reference image with the control image, and thus to be able to assess physiological effects of laser irradiation on the fundus of the eye.

Figure 3:
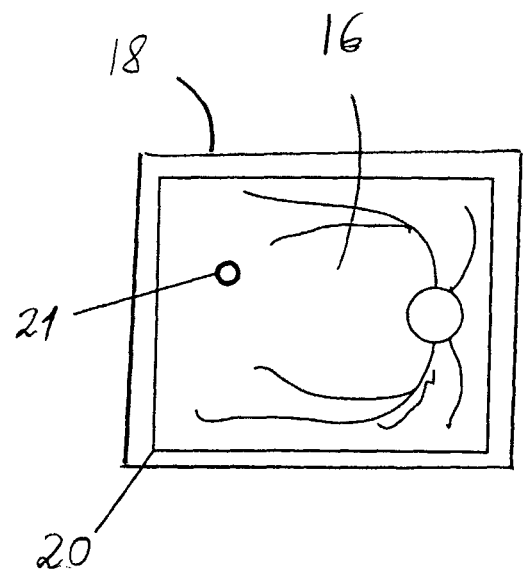
FIG. 3 is a schematic representation of a reference image.

FIG. 3 is a schematic representation of an exemplary control image 20 which has been taken according to the method described on the basis of FIG. 2, for example, and is represented on a screen 18 of an ophthalmoscope of the type proposed herein, such as the embodiment 1 described on the basis of FIG. 1. This control image has been taken using illumination with visible light such that it comprises color information of the fundus of the eye 16. In particular, lesion 21 can be made out as bleaching which has been caused by laser irradiation of the fundus of the eye 16.

The control image 20 could have been generated either in a purely diagnostic control examination of the eye 4 according to a method described above wherein the lesion 21, for example, has been caused during a treatment session already completed. The control image 20 shown in FIG. 3 can also be generated during a laser treatment. Then, the control image 20 is preferably displayed on the screen 18 immediately after the generation thereof. After actuating a control element 9 of the ophthalmoscope or later after the course of a control time lasting 5 seconds in this embodiment this control image 20 will be faded out again. Before and after the control image 20 a continuous real time image of the fundus of the eye 16 generated using an infrared illumination is shown.

Figure 4:
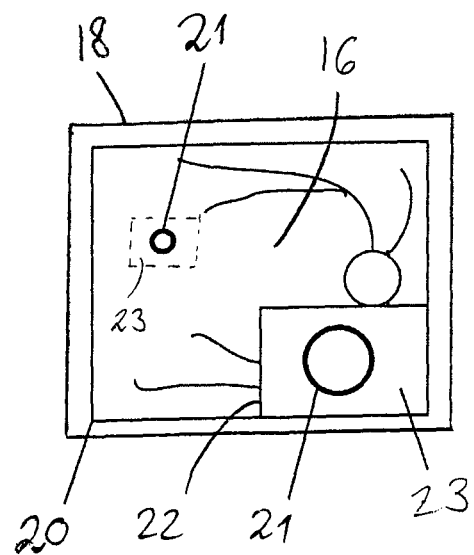
FIG. 4 is a schematic representation of a reference image with an additionally inserted image detail.

FIG. 4 schematically shows a control image 20 again which differs from the control image described according to FIG. 3 only in an image detail 22 superimposed in addition which partly superimposes the control image 20. For the generation of this image detail 22 the image processing unit 10 selects an image area 23 of the control image comprising the lesion 21, magnifies this image area 23 and superimposes the control image partly with the image area 23.

Figure 5:
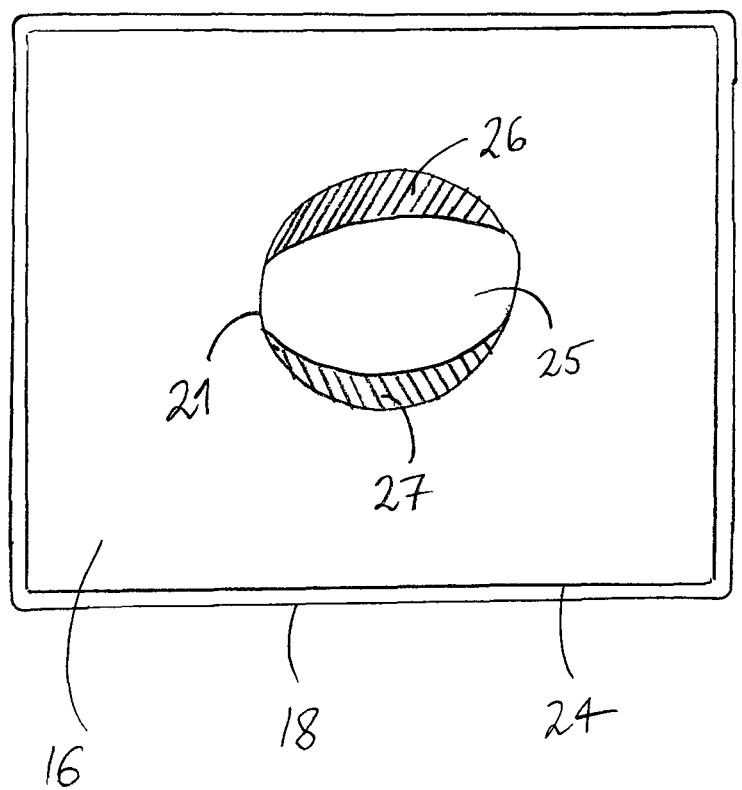
FIG. 5 is a schematic representation of a difference image.

In FIG. 5, there is schematically shown a difference value image 24 of the type proposed herein which has been generated from a control image and a reference image, for example, which in their turn have been taken according to a method described on the basis of FIG. 2. For the generation of the difference value image 24 such as by means of the embodiment 1 of the invention described on the basis of FIG. 1, the reference image and the control image are linked together by means of feature based image registration. Subsequently, the difference values between pixel values of the reference image and the control image are calculated. An intermediate image (not shown herein) generated from these difference values is segmented on the basis of three predetermined value ranges into image segments which will be allocated to a first, a second and a third segment class on the basis of the respective value ranges. Then, an image segment of the first segment class means a treatment success within that image segment, an image segment of the second segment class means necessary repetition of the treatment within that image segment, and an image segment of the third class means necessary reduction of laser intensity within that image segment. Finally, the difference value image is displayed in a monochrome representation or a false color representation on a screen 18 of the observation device 17.

Thus, when performing a treatment of the fundus of the eye 16 by means of an ophthalmoscope described on the basis of FIG. 1, for example, the target laser beam 11 is positioned onto a region of the fundus 16 of the eye to be treated by means of the laser guiding device 3. Then, using infrared illumination of the eye 4, the fundus as well as the target laser beam are observed as a real time image on the screen 18 of the observation device 17. Subsequently, irradiation with the therapeutic laser beam 11 is released by the control unit 8. At defined moments before and after the eye irradiation with the therapeutic laser beam 11 the eye 4 will be illuminated each in short-duration with a light pulse of visible light. Moreover, the control images acquired by the camera 6 during these both light pulses are read out from the camera 6 as has been described on the basis of FIG. 2. Subsequently, the difference value image 5 described above is created from the both control images by means of the image processing unit 10 being configured appropriately, and displayed on the screen 18 of the observation device.

In the present embodiment the illustrated difference image 24 comprises three image segments 25, 26, 27 wherein the first image segment 25 belongs to the first segment class, the second image segment 26 belongs to the second segment class and the third image segment 27 belongs to the third segment class. From this exemplary difference value image a physician treating the patient extracts about the lesion 21 information that the region of the fundus of the eye 16 to be treated has been successfully irradiated within the image segment 25 whereas irradiation within the image segment 26 was insufficient (and possibly should be repeated), and that in the third image segment the laser intensity was selected excessively.

According to such an interpretation of the difference value image 24 the real time image of the fundus of the eye using infrared illumination is displayed again wherein a changeover to the real time image is carried out either by the physician through the input interface 9 or automatically after a predetermined control time amounting to 5 seconds in the present embodiment.

In an alternative embodiment of the last described method the control image 18 described on the basis of FIG. 3 or FIG. 4 is displayed instead of the difference value image 4. In another embodiment of the method the control image 18 or the difference value image 24 is carried out only after a predetermined number of performed laser irradiations of the eye 4 for acceleration of the method. In an appropriate difference value image 24 or control image 18 several lesions can then be diagnosed simultaneously. In further advantageous embodiment, through the input of respective commands by means of the user interface 9 the physician treating the patient selects between the described representations of fundus of the eye 16 through the control images 18 or through the difference value image 24 described on the basis of FIG. 3 and FIG. 4.

Such a treatment method in particular by means of an ophthalmoscope of the type proposed herein has the advantage that individual process steps of an eye treatment by means of laser irradiation can be automated superiorly such as through the described superimposing and fading out of control images or difference value images immediately after the application of laser irradiation. Such automation accelerates the course of treatment particularly with a great number of laser treatments to be carried out individually in a panretinal application, and facilitates manipulation and control of the ophthalmoscope simultaneously.

The present invention is thus based on the object to propose an ophthalmoscope solving or at least moderating the above problems which is thus suitable for a reduction of unintended ocular movements during eye monitoring and in particular during a laser treatment of the eye. Furthermore, the object is to propose a respective method of observation of an eye, in particular for controlling a therapeutic treatment of an eye region, and finally to propose a method of performing a laser treatment solving or at least moderating the problem of unintended ocular movements.

This object is solved according to the invention by means of an ophthalmoscope and a method in accordance with the independent claims as well as by means of a method according to claim 13. Further developments of the invention are subject-matter of the sub-claims.

Thus, an ophthalmoscope according to the invention having a laser device for laser irradiation of an eye, in particular to perform a photocoagulation on a fundus of the eye, comprises an illuminator for illuminating the eye as well as a camera for acquiring an image of the eye, wherein the illuminator is adapted to generate visible and infrared light, the ophthalmoscope further comprising a control unit which is adapted to trigger the illuminator for generating a light pulse of visible light, and to read out from the camera a control image of the eye acquired by the camera during the light pulse.

The ophthalmoscope according to the invention having the laser device is suitable for acquiring an image of the eye, particularly of a fundus of the eye, during illumination of the eye with a light pulse of visible light. By preferably being as short as possible the light pulse does not result in any dazzling, or only in negligible dazzling, of the eye, and does not result in any or only in a slight contraction of a pupil of the eye during examination or laser treatment of the eye.

Preferably, the light pulse has a wide frequency spectrum in order to enable a control image in color that is as detailed as possible. Alternatively, it also can be provided that the light pulse comprises only a predetermined narrow section of the visible frequency spectrum in order to examine a specific layer depth of the eye tissue. In this manner, it is particularly possible to separately analyze a physiological effect of a laser treatment, such as of a fundus of an eye, within different layer depths according to wave lengths of the light pulse. To this end, the illumination apparatus preferably comprises one or a plurality of light sources, such as light emitting diodes, which are each suitable for generating light within a narrow frequency range.

In an alternative embodiment the control unit is adapted to trigger the illuminator for generating a light pulse within an infrared frequency range, and to read out from the camera a control image of the eye acquired by the camera during the light pulse. As a result, this embodiment is suitable for forming an image of structures in a greater depth within the tissue of the eye than is possible with visible light. Generally, the tissue structures can be imaged with light approximately within a penetration depth of the light into the tissue. Since the penetration depth scales with the wavelength of the light, infrared light in particular has a greater penetration depth than visible light.

Moreover, the camera preferably is a color picture camera with a resolution as high as possible which for example is equipped with a CCD sensor. In another embodiment the ophthalmoscope comprises an observation device preferably having a screen which is connected to the camera for observing the images of the eye acquired by the ophthalmoscope.

It is particularly advantageous if the camera is sensitive to infrared light in addition to visible light. Because infrared light is not discerned by the human eye, the eye may be continuously irradiated with infrared light during the examination without dazzling the patient. In this way, a continuous sequence of eye frames, hereinafter also termed real time image, can be generated with the ophthalmoscope during the examination or treatment of the eye. Although some details of fundus of the eye are not discernible when using infrared illumination, such as lesions of the retina due to laser irradiation, the real time image generated using infrared illumination permits a continuous observation of the eye without any adverse dazzling effect, and thus in particular a safe positioning of a target laser beam on a region to be treated in the fundus of the eye.

In a further development of the ophthalmoscope it is provided that the control unit is adapted to trigger the illuminator for generating the light pulse after a predetermined waiting time interval after laser irradiation of the eye and to read out from the camera the control image acquired by the camera during the light pulse. The waiting time interval is preferably selected to be so long that physiological processes induced by the laser irradiation, such as for example denaturation of proteins within the irradiated tissue, are largely finished so that a maximally reliable evaluation of success of the irradiation is feasible on the basis of the control image. The waiting time interval is preferably in a range between 1 millisecond and 5 seconds, most preferably in a range between 40 milliseconds and 1 second.

In an alternative embodiment of the invention the control unit is adapted to trigger the illuminator for generating the light pulse after a predetermined waiting time interval after the completion of a series of a predetermined number of individual laser irradiations and to read out from the camera the control image acquired by the camera during the light pulse. In this manner, quick performance of laser treatment is achievable, in particular when a great number of individual laser irradiations (laser pulses) have to be applied. This waiting time interval is again preferably within the ranges indicated above.

In a further development of the ophthalmoscope according to the invention it is provided that the control unit is adapted to trigger the illuminator for generating the light pulse a predetermined time interval before laser irradiation, and to read out from the camera a control image acquired by the camera during the light pulse as a reference image. Such a reference image has the advantage of being superiorly suitable for comparison with a control image acquired by the camera immediately after the respective laser irradiation during the light pulse because both control images were preferably generated within a maximally short time span (which is the sum of said time interval, a laser pulse duration and the waiting time interval defined above), and the eye probably did not, or only slightly, move within this time span. This permits a superior image registration (see below) of the reference image (before laser treatment) with the control image (after laser treatment). Said time interval is preferably in a range between 5 s and 40 ms, most preferably in a range between 200 ms and 40 ms.

In a further development of the invention, there is provided that the control unit is connected to an input interface for inputting a trigger signal wherein the control unit is adapted to trigger the illuminator for generating the light pulse after inputting the trigger signal, and to read out from the camera the control image acquired by the camera during the light pulse. In this manner, a physician treating the patient can generate a control image at any time during the examination or treatment, preferably in the form of a color snapshot, without unnecessarily severe dazzling of the patient.

In a further development of the ophthalmoscope according to the invention it is provided that it comprises a digital image processing unit connected to the camera which is adapted to generate a difference value image from a pair of control images. To this end, the image processing unit is equipped with a memory to store the control images, and further adapted to perform a preferably feature based image registration of these both control images so that ocular movements occurring in an interval between shooting both control images can be eliminated. In a simplified embodiment the image processing unit is adapted to use for generating the difference value image, instead of such an image registration, only such image points of both control images between which no ocular movement has taken place and which thus are congruent to each other.

The difference value image consists of pixel values which each image a difference value each defined by a difference between associated pixel values of both (image registered) control images. Such a difference value image is advantageous in that distinctions between both control images are superiorly discernible on it and are quantifiable. Here, the first of both control images preferably is a reference image described above which has been taken before laser irradiation and buffered in the memory, and the second reference image preferably is a control image which has been taken after this laser irradiation. On the basis of such a difference value image the physiological effect, and thereby the therapeutic success of these individual laser irradiations of the eye, can be assessed and quantified in a particularly reliable manner.

In a further development it is provided that the image processing unit is adapted to segment the difference value image according to predetermined value ranges for difference values of the difference value image in order to achieve a representation of the difference value image which is particularly clear and easy to be interpreted. Preferably, the image processing unit is adapted to segment the difference value image into segments of a first, a second and a third segment class wherein an image segment of the first segment class signals a treatment success within this image segment, an image segment of the second segment class signals a necessary repetition of the treatment within that image segment, and an image segment of the third segment class signals a necessary reduction of a laser intensity within that image segment. In this manner, it is possible for a physician treating the patient to decide at a glance whether laser irradiation which was applied between both control images which form a part of the difference value image was successful in the desired degree, whether it should be repeated or whether the laser intensity for the respective range has to be adapted.

In a further development of the invention it is provided that the image processing unit is adapted to select and magnify an image detail of a control image, and to partly superimpose the control image with the selected and magnified image detail wherein the selected and magnified image detail includes a region of the eye treated with laser irradiation. The image detail selected, magnified and superimposingly fitted into the control image serves to produce a particularly distinct representation of details of the treated region of the eye and to better assess a physiological effect of laser irradiation of the region. In an alternative embodiment of the invention the control unit is adapted to generate for the selected image detail a difference value image, preferably with a corresponding image detail of a second control image acquired by the camera immediately before laser irradiation during a light pulse as described above, subsequently to magnify this difference value image and to partly superimpose the control image with this difference value image.

In a further development of the ophthalmoscope according to the invention it is provided that the laser device comprises a beam guiding unit for the guidance of a laser beam generated by the laser device. Such an ophthalmoscope is suitable for positioning the laser beam on a desired region of the eye. To this end, the laser device is preferably adapted to generate a target laser beam having reduced intensity which does not have any or only insignificant physiologic effects on the tissue of the eye. Preferably, this beam guiding unit is adapted to guide the laser beam out of an observation range of the camera during the light pulse of visible light. In this manner, it is particularly achieved that during the acquisition of a control image before or after laser irradiation of a treatment region the target laser does not irradiate it any longer, and thus also does not obscure the image information from the treatment region. Such guiding out, and preferably subsequent guiding back, of the target laser beam has the advantage of being feasible within a very short time interval, whereas completely deactivating and subsequently reactivating the laser requires an intervening break.

In a further development, the ophthalmoscope comprises an indicating device for representing, in a range visible to the eye (to be examined or to be treated), a fixation point to focus the eye onto the fixation point whereby instinctive ocular movements can be additionally counteracted.

The method according to the invention for acquiring a control image of an eye is performed with an ophthalmoscope of the type described herein, an illumination of the eye with visible light being carried out with a duration as short as possible for a simultaneous shot of a control image with the camera, whereby instinctive ocular movements of the patient due to dazzling of the patient can be largely prevented. Preferably, a continuous observation of the eye using infrared illumination of the eye is carried out wherein image signals of the camera are forwarded to an observing apparatus, for example an apparatus having a screen. Moreover, the method according to the invention for the laser treatment of an eye with an ophthalmoscope, in particular for the execution of photocoagulation of the fundus of the eye, provides that laser irradiation of the eye is carried out with a laser device of an ophthalmoscope, and after a predetermined waiting time interval after the laser irradiation the eye is illuminated with a light pulse by an illuminator of the ophthalmoscope of visible light, and simultaneously a control image of the eye is acquired with a camera of the ophthalmoscope. During the treatment the eye is preferably observed continuously using infrared illumination. The methods are furthermore preferably carried out with an ophthalmoscope of the type proposed herein.

Dosing laser irradiation on the retina:

Generally the energy density necessary to achieve a given effect (denaturization) on the retina is strongly dependent e. g. on ethnicity (strong pigmentation vs. light pigmentation) but may even vary in a single eye since the pigmentation in the periphery of the retina is much less than in the central area. In the state of the art the surgeon needs to manually adjust the relevant parameters of the photocoagulation light source (typically a laser source) according to the effect on the tissue that he determines subjectively under white light illumination. The degree to which the surgeon actually adjusts the treatment to the varying tissue properties depends on Experience and level of training of the surgeon,
Compliance of the patient,
Available time and other factors.

In order to probe the tissue properties the surgeon typically places a few lesions in non-critical areas of the retina subjectively determining suitable laser parameters.

In order to achieve a consistent treatment effect across a number of patients it is important to reproducibly create the same effect on the tissue independently from varying tissue properties.

The proposed apparatus can provide exactly that by
  Applying a probe pattern of laser pulses with varying parameters for each single laser pulse in order to determine the optimum laser parameters.
  The apparatus hereby obtains the optimum laser parameters by interpolation between the results determined from discrete measurements with different sets of laser parameters.
  Storing the laser parameters which were used to create the optimum effect with respect to landmarks determined from recorded images (e. g. when creating test lesions at different locations on the tissue). Either the operator himself determines the optimum parameters and selects them to be stored to the control unit or the optimum parameters are automatically determined from pre-defined thresholds of the changes in the tissue. The optimum parameters are then suggested to the operator prior to treatment of a specific location on the retina.
  The apparatus creates a map of optimum laser parameters by spatially interpolating between the probe lesions. When the surgeon moves the aiming beam to a different location on the tissue the apparatus then suggests optimized laser parameters according to the stored parameter map.
  The apparatus improves the map of optimum laser parameters with each lesion created by the surgeon using the methods described above.
  Lesion assessment during laser emission:

The exposure time of the camera may be well below the duration of the treatment laser emission, e. g. in the range of 1 ms . . . 40 ms. It is also feasible to entirely block emissions from the treatment laser to reach the imaging camera using suitable filters.

An advantageous embodiment of the invention records images during application of treatment light. In this way the effect on the tissue can be assessed during the laser emission and not only after a set pulse duration. The laser emission may be interrupted by the control unit when a given effect on the tissue is created and therefore overtreatment is avoided.

Novel Laser Treatment Methods Using Short Pulse Trains:

Novel laser treatment methods aim at destroying as little tissue as possible while achieving the maximum positive effect on the pathologic condition of the tissue. Some of these ideas are based on local and reversible tissue heating while coagulation is based on permanent denaturization of proteins. Typically, short laser pulses of durations in the range of picoseconds to milliseconds are applied in long pulse trains of milliseconds to seconds duration. In contrast to the conventional photocoagulation it is not desired to create visible lesions. As with conventional photocoagulation the dosing of laser irradiation is difficult due to a priori unknown tissue properties.

The proposed apparatus can be used to apply pulse trains with the least damaging effect on the retina possible by
  Applying the train of laser pulses,
  Acquiring images during the application of said pulse train,
  Determining if any changes in the tissue have taken place at the given location of laser application with respect to a reference image,
  Interrupting the pulse train as soon as changes in the tissue are detected according to pre-set thresholds.

In another embodiment of the invention the application of the pulse train is temporarily interrupted when an image is acquired which is used to determine a change in the tissue. This is particularly beneficial if light emitted by the treatment laser may impinge on the imaging sensor. After determination of the tissue effect the laser emission is continued at the same location on the retina. If an effect on the tissue was determined the treatment at said location is marked as successful.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. An ophthalmoscope having a laser device for laser treatment of a fundus of an eye, the ophthalmoscope comprising:
  an illuminator for illuminating the fundus of the eye with an invisible infrared illumination beam and with a light pulse of visible light;
  a camera, sensitive to infrared light and visible light, configured for acquiring images of the fundus of the eye;
  a control unit, operatively connected to the illuminator and to the camera, configured for triggering the illuminator to generate the infrared illumination beam and for reading out from the camera a sequence of infrared images of the fundus of the eye acquired by the camera during the illumination with the infrared illumination beam, the control unit further configured for triggering the illuminator to generate the light pulse of visible light, and for reading out from the camera at least one control image acquired by the camera during the light pulse of visible light; and
  an observation device with a screen configured for displaying the sequence of infrared images as an infrared real time image of the fundus of the eye,
  wherein the control unit is configured to automatically trigger the illuminator to generate the light pulse and to read out the control image from the camera during laser irradiation or at an instance of time which is a predetermined waiting time interval after laser irradiation, and
  wherein the control unit is configured to determine a bleaching effect of the laser irradiation on a laser irradiated location of the fundus on the basis of the control image and to automatically interrupt further laser irradiation of the laser irradiated location of the fundus when the bleaching effect of the laser irradiation on the laser irradiated location of the fundus has reached a pre-set bleaching threshold.

2. The ophthalmoscope of claim 1, wherein the control unit is configured to automatically trigger the illuminator to generate the light pulse and to read out the control image from the camera at the instance of time which is a predetermined waiting time interval after completion of a series of a predetermined number of individual laser irradiations.

3. The ophthalmoscope of claim 2, wherein the control unit is configured to automatically trigger the illuminator to generate a further light pulse a predetermined time interval before the laser irradiation and to read out a reference image from the camera acquired by the camera during the further light pulse of visible light.

4. The ophthalmoscope of claim 1, wherein the ophthalmoscope includes an image processing unit connected to the camera, the image processing unit configured to generate a difference value image from the reference image and the control image acquired by the camera.

5. The ophthalmoscope of claim 4, wherein the image processing unit is configured to segment the difference value image according to predetermined value ranges for difference values of the difference value image.

6. The ophthalmoscope of claim 4, wherein the image processing unit is configured to segment the difference value image into image segments of a first, a second and a third segment class, wherein an image segment of the first segment class signals a treatment success within the image segment, an image segment of the second segment class signals a necessary repetition of the treatment within the image segment, and an image segment of the third segment class signals a necessary reduction of a laser intensity within the image segment.

7. The ophthalmoscope of claim 4, wherein the image processing unit is configured to select and magnify an image detail of the control image and to partly superimpose the control image with the selected and magnified image detail, and wherein the selected and magnified image detail includes a treated region of the eye.

8. The ophthalmoscope of claim 1, wherein the laser device includes a beam guiding unit for guiding a laser beam generated by said laser device.

9. The ophthalmoscope of claim 8, wherein the beam guiding unit is configured to guide the laser beam of the laser device from an observation range during the light pulse of visible light.

10. The ophthalmoscope of claim 1, wherein the illuminator includes at least one light emitting diode.

11. The ophthalmoscope of claim 1, wherein the treatment comprises a photocoagulation on the fundus of the eye.

12. A method for laser treatment of a fundus of an eye of a patient, the method comprising:
illuminating the fundus of the eye with invisible, infrared light by means of an illuminator and generating a sequence of infrared images of the fundus of the eye under the infrared illumination by means of a camera, the camera being sensitive to infrared light and to visible light, and displaying the sequence of infrared images on a screen as an infrared real time image to allow for a continuous observation of the fundus of the eye;
laser irradiating the fundus of the eye with a treatment laser device concurrently with the acquisition of the sequence of the infrared images;
automatically triggering the illuminator to generate, at an instant of time which is during laser irradiation or at an instance of time which is a predetermined waiting time interval after the laser irradiation, a light pulse of visible light illuminating the fundus of the eye with the light pulse;
acquiring a control image of the fundus of the eye with the camera during the light pulse;
controlling a bleaching effect of the laser treatment at a laser irradiated location of the fundus of the eye on the basis of the control image; and
automatically interrupting further laser irradiation of the laser irradiated location of the fundus when the bleaching effect of the laser irradiation on the laser irradiated location of the fundus has reached a pre-set bleaching threshold.

13. The method of claim 12, wherein the illuminator is triggered and the control image is acquired at an instance of time which is after a predetermined waiting time interval after completion of a series of a predetermined number of individual laser irradiations.

14. The method of claim 12, further comprising generating a difference value image from the reference image and the control image acquired by the camera.

15. The method of claim 14, further comprising segmenting the difference value image according to predetermined value ranges for difference values of the difference value image.

16. The method of claim 14, further comprising segmenting the difference value image into image segments of a first, a second and a third segment class, wherein an image segment of the first segment class signals a treatment success within the image segment, an image segment of the second segment class signals a necessary repetition of the treatment within the image segment, and an image segment of the third segment class signals a necessary reduction of a laser intensity within the image segment.

17. The method of claim 12, further comprising:
selecting and magnifying an image detail of the control image, the selected and magnified image detail includes a treated region of the eye; and
superimposing a portion of the control image with the selected and magnified image detail, wherein the selected and magnified image detail includes a treated region of the eye.

18. The method of claim 12, further comprising guiding a laser beam generated by the laser device from an observation range during the light pulse of visible light.

19. The ophthalmoscope of claim 1, wherein the predefined waiting time interval has a length between 1 millisecond and 5 seconds.

20. The ophthalmoscope of claim 1, wherein the predefined waiting time interval has a length between 40 milliseconds and 1 second.

21. The ophthalmoscope of claim 3, wherein the predefined time interval has a length between 40 milliseconds and 5 seconds.

22. The ophthalmoscope of claim 3, wherein the predefined time interval has a length between 40 milliseconds and 200 milliseconds.

23. The method of claim 12, wherein the predefined waiting time interval has a length between 1 milliseconds and 5 seconds.

24. The method of claim 12, wherein the predefined waiting time interval has a length between 40 milliseconds and 1 second.

25. The method of claim 12, further comprising;
automatically triggering the illuminator to generate, at one further instant of time which is a predetermined time interval before the application of the at least one laser pulse onto the one treatment zone, a further light pulse of visible light illuminating the fundus of the eye with the further light pulse;
acquiring a reference image of the fundus of the eye with the camera during the further light pulse; and
controlling the effect of the laser treatment on the treatment region of the fundus of the eye by comparing the control image with the reference image.

26. The method of claim 12, wherein the fundus of the eye is photocoagulated by the laser irradiation.

27. An ophthalmoscope having a treatment laser device for applying treatment laser pulses onto a fundus of an eye, the ophthalmoscope comprising:

an illuminator for illuminating the fundus of the eye with an invisible infrared illumination beam and with a light pulse of visible light;

a camera, sensitive to infrared light and visible light, configured for acquiring images of the fundus of the eye;

a control unit, operatively connected to the illuminator and to the camera, configured for triggering the illuminator to generate the infrared illumination beam and for reading out from the camera a sequence of infrared images of the fundus of the eye acquired by the camera during the illumination with the infrared illumination beam; and an observation device with a screen configured for displaying the sequence of infrared images as an infrared real time image of the fundus of the eye, wherein the control unit is configured to automatically trigger, at an instance of time which is during laser irradiation or which is a predetermined waiting time interval after applying a treatment laser pulse onto the fundus, the illuminator to generate a light pulse of visible light and to read out a control image from the camera a control image acquired by the camera during the light pulse of visible light, wherein the control unit is configured to determine, on the basis of the control image, a bleaching effect caused by the treatment laser pulse on a location of the fundus irradiated by the treatment laser pulse, and wherein the control unit is configured to automatically interrupt laser irradiation or prevent application of further laser pulses onto the irradiated location of the fundus when the determined bleaching effect has reached a pre-set bleaching threshold.

* * * * *